United States Patent [19]

Joseph

[11] Patent Number: 4,644,782
[45] Date of Patent: Feb. 24, 1987

[54] SPINNING ROD INTERFACIAL TENSIOMETER

[75] Inventor: Daniel D. Joseph, Minneapolis, Minn.

[73] Assignee: Regents of the University of Minnesota, Minneapolis, Minn.

[21] Appl. No.: 829,416

[22] Filed: Feb. 13, 1986

[51] Int. Cl.[4] .......................................... G01N 13/02
[52] U.S. Cl. ................................................. 73/64.4
[58] Field of Search ...................................... 73/64.4

[56] References Cited

U.S. PATENT DOCUMENTS 4,250,741  2/1981  Scriven, II et al. ................. 73/64.4

FOREIGN PATENT DOCUMENTS 2916027  10/1980  Fed. Rep. of Germany ....... 73/64.4

OTHER PUBLICATIONS

Fink et al., "Multicell Spinning Drop Interfacial Tensiometer," *Rev. Sci. Instrum.* 49(2), Feb. 1978, pp. 188–193.

Joseph, Daniel D., Y. Renardy, M. Renardy and K. Nguyen, "Stability of Rigid Motions and Rollers in Bicomponent Flows of Immiscible Liquids," *J. Fluid Mech.*, vol. 153, pp. 151–156 (1985).

*Primary Examiner*—Stewart J. Levy
*Assistant Examiner*—John E. Chapman, Jr.
*Attorney, Agent, or Firm*—Kinney & Lange

[57] ABSTRACT

A transparent cylinder is filled with two liquids of different densities and is sealed at both ends. A rod, having a diameter smaller than the inner diameter of the cylinder is mounted on the longitudinal axis of the cylinder. The filled cylinder is mounted horizontally between two end supports and rotated about the longitudinal axis of the cylinder. The less dense liquid will form around the rod at an appropriate speed, and when steady state equilibrium is achieved by the liquids inside the cylinder, the diameter of the less dense liquid and the rotational speed of the cylinders are measured.

15 Claims, 7 Drawing Figures

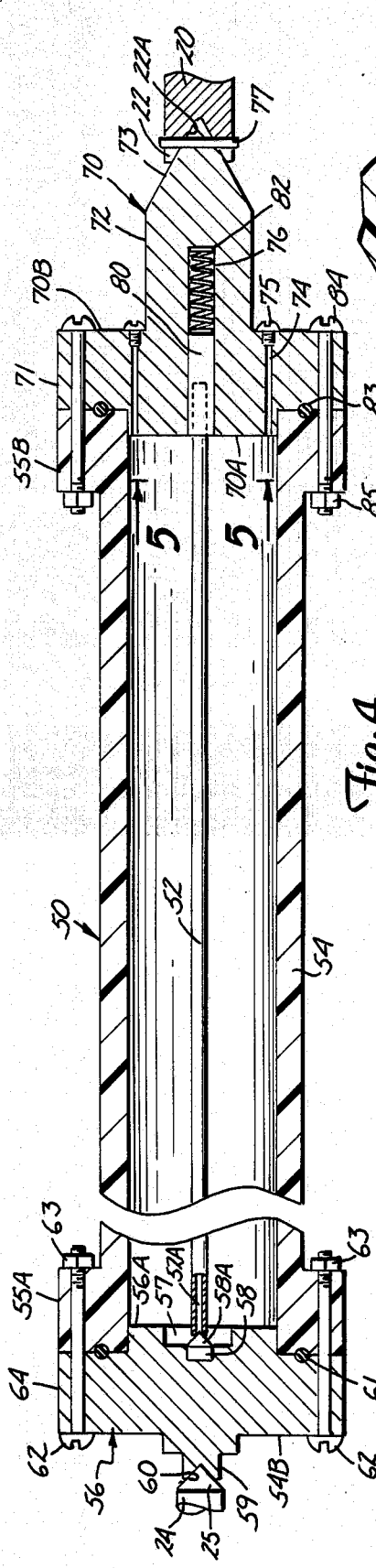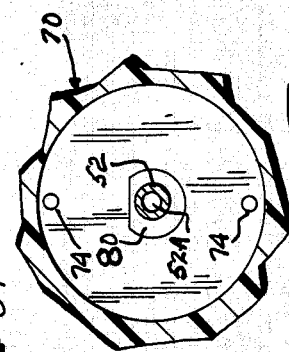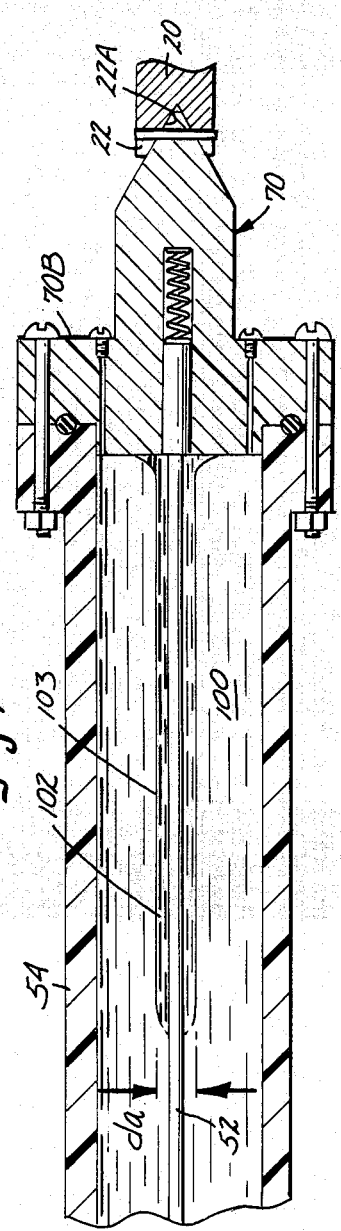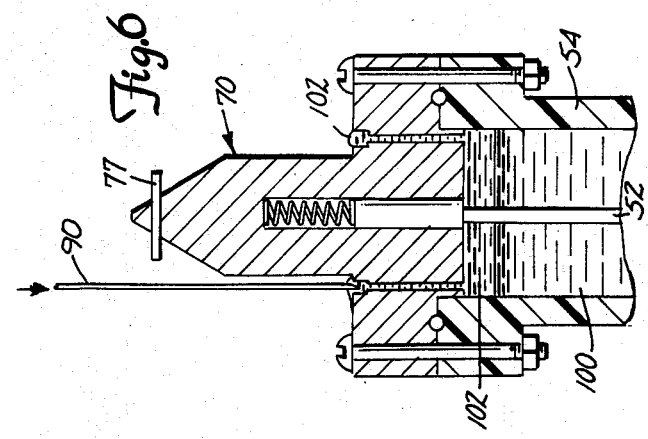

SPINNING ROD INTERFACIAL TENSIOMETER

BACKGROUND OF THE INVENTION

1. Field of the Invention

The present invention is an improved apparatus for measuring the interfacial tension between two liquids having different densities.

When two immiscible liquids are in contact, the work required by the molecules to reduce their respective surface areas is conventionally known as interfacial tension. Interfacial forces govern such phenomena as the wetting or nonwetting of solids by liquids and the capillary rise of liquids in fine tubes and wicks. The measurement of interfacial tension is important to several technologies and industrial applications, including detergents, anti-frothing agents and soaps.

2. Description of the Prior Art.

An instrument for measuring interfacial tension between two fluids is disclosed in U.S. Pat. No. 4,250,741 issued to Scriven, II et al. The Scriven instrument is based upon the spinning drop technique, one of the conventional shape methods of the known art for measuring fluid interfacial tension. The Scriven instrument includes a sample tube for containing the fluids and a hosuing for enclosing the tube. A massive bearing housing contains a precision ground shaft and is connected to the sample tube. The shaft is rotated by a motor causing the tube to rotate at the same rate.

To measure interfacial tension between two fluids with the Scriven device, a single drop of the less dense fluid is loaded into a tube filled with the more dense fluid. The tube is spun until gyrostatic equilibrium is reached and the drop migrates to an ever-so-slightly elevated end of the tube for viewing. Typically, a drop takes four to six hours to migrate to the desired position. In some cases, the drop may be kept spinning for days. Compressed air is forced into the bearing housing to maintain temperatures during operation of the instrument. When all required conditions are met, the apparent drop diameter is measured by a microscope and the rotational speed of the drop is recorded.

The Scriven device has several drawbacks. First, the Scriven tensiometer requires specially constructed equipment and parts. Second, interfacial tension measurements can require a great deal of time and skill. Third, loading the fluids in the sample tube can be difficult, particularly when attempting to keep the drop of lighter fluid away from the sides of the tube. Further, if the drop assumes an oblong shape at the time the diameter is measured, inaccurate results may result.

The theory for the present device was developed in an article by Joseph et al (D.D. Joseph, Y. Renardy, M. Renardy and K. Hguyen, 153 *J. Fluid Mech.* 151 (1985)). The article considered the flow of two immiscible liquids of different viscosities and densities rotated between concentric cylinders. The interface between the two fluids has a constant radius when the density difference, represented by [$\rho$], is positive, and when the more dense fluid is centrifuged to the outer portions of the outer cylinder. The relationship between interfacial tension T and the radius of the interface r is expressed as:

$$([\rho]r^3\Omega^2)/T \geq 4 \qquad (1)$$

where, $\Omega$ is the angular velocity of the cylinders around the axis of symmetry.

The inequality (1) does not hold for free drops. When $\Omega$ is large, the free drop is cigar shaped, and a constant d appears only in an approximate sense. As $\Omega$ is increased the drop will elongate and its radius (r) will decrease in such a way that $$([\rho]r^3\Omega^2)/T = 4 \qquad (2)$$

approximately. Equation (2) is the basis of both the spinning drop and the spinning rod tensiometer. If the drop is kept from elongating, say by blocking the elongation with end plates perpendicular to the axis of rotation, then a constant radius can be achieved. Further increases of $\Omega$ do not change the shape of the interface and the inequality (1) is appropriate.

SUMMARY OF THE INVENTION

The present invention relates to an apparatus for measuring the interfacial tension between two immiscible liquids. The proportions of the two liquids used in the apparatus are not critical. The measurements can be made shortly after the apparatus is engaged.

A transparent tubular cylinder for receiving two liquids of different densities is sealed at both ends. A rod, having a diameter smaller than the inner diameter of the cylinder is mounted on the longitudinal axis of the cylinder. This forms an annular chamber surrounding the rod within the cylinder. The liquids are added to the annular chamber and then the cylinder is mounted horizontally between two end posts and rotated about the longitudinal axis of the cylinder. When an appropriate steady state equilibrium is achieved by the liquids inside the cylinder, the apparent dimaeter of the less dense liquid and the rotational speed of the cylinder are measured. The radius is obtained by dividing the diameter by two.

The apparatus is of simple and robust construction, and does not require sophisticated technology nor expensive materials. The spinning rod tensiometer is an economical and accurate device for measuring interfacial tension.

BRIEF DESCRIPTION OF THE DRAWINGS

FIG. 4 is a fragmentary sectional view of a cylinder assembly used with the apparatus of FIG. 1 and taken along line 4—4 in FIG. 3.

FIG. 5 is a sectional view taken along line 5—5 of FIG. 4.

FIG. 6 is a sectional view of one end of the cylinder assembly of FIG. 4, showing a method of injecting liquid into the cylinder using a hypodermic needle.

FIG. 7 is a fragmentary sectional view taken on the same line as FIG. 4, showing the cylinder assembly after the two test fluids have been added and after the cylinder has been rotated to achieve steady state equilibrium inside the cylinder assembly.

DETAILED DESCRIPTION OF THE PREFERRED EMBODIMENTS

Figure 1:
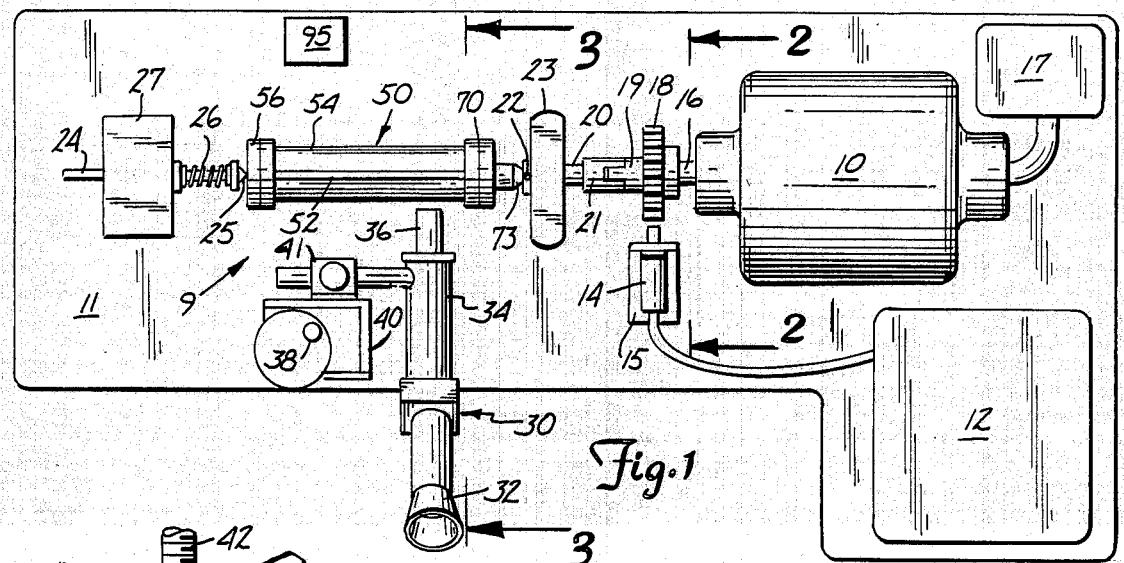
FIG. 1 is a top plan view showing an apparatus made according to the present invention and used for testing interfacial tension.

The instrument of the present invention is shown generally at 9 in FIG. 1, and includes an electric drive motor 10 mounted on a base 11. It is preferred that the motor 10 has a top speed of more than 5000 rpm and that the base 11 be as rigid as possible to avoid vibrations. A speed controller 17 for adjusting the speed of the motor 10 is connected to the motor 10. The shaft 16 of the motor 10 has a spur gear 18 mounted about it. A male coupling member 19 is mounted on the shaft 16 and drivably mates with a complementary drive coupling member 21 mounted on one end of a short shaft 20.

Shaft 20 is rotatably mounted in a shaft support column 23 fixed to the base 11. The shaft 20 is freely rotatable in the support column 23. At the end of the shaft 20 opposite the coupling 21, an axial drive slot 22 intersects a conical recess 22A (see FIG. 7) formed in the shaft 20.

Figure 2:
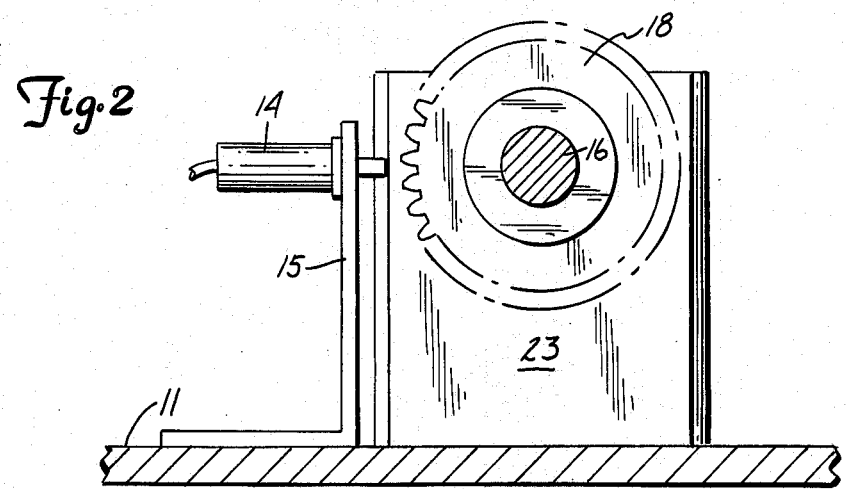
FIG. 2 is a sectional view taken along line 2—2 of FIG. 1.

As can be seen best in FIG. 2, a shaft speed transducer 14 is mounted on a support 15 and placed substantially perpendicular to the gear 18. The transducer 14 measures the speed of rotation of the gear 18 by sensing the teeth. It is preferred that the transducer 14 be of the conventional photoelectric cell type to project a beam of light on the teeth, receive a reflected beam and produce an electrical signal. A counter 12 receives the signal from the transducer 14 and displays the speed of the gear 18.

A cylinder assembly 50 having an outer tubular cylinder 54 and a tubular inner rod 52 (shown in partial section in FIG. 4) is horizontally mounted between the shaft 20 and a tail stock type plunger which is mounted on and axially slidable within a support column 27. The support column 27 is fixed to base 11. At the end of the plunger 24 closest to the cylinder assembly 50, a conical centering tip 25 is provided. A coil spring 26 is mounted axially along the plunger 24 so that the spring 26 urges the tip 25 away from the support column 27.

To measure interfacial tension between two fluids of different densities, the cylinder assembly 50 is inserted between the shaft 20 and the plunger 24. As the cylinder assembly 50 is positioned in place, the spring 26 urges the conical tip 25 into a conical recess 60 in a tip 59 fixed to the end cap 56 of the cylinder assembly 50. At the opposite end of the cylinder assembly 50, a loading cap 70 fixed to the cylinder assembly 50 has a conical tip 73 which is inserted into the conical recess 22a in the end 22 of the shaft 20. A cross pin 77 is mounted in the tip 73 and drivably engages the slot 22.

When the motor 10 is operated, the coupling 19 transfers the angular velocity of the shaft 16 to the coupling 21 and shaft 20. The slot 22 of the shaft 20 transmits the angular velocity of the shaft 20 to the cylinder assembly 50. The cylinder assembly 50 is thus horizontally supported and is rotatable between supports 23 and 27 under control of the motor 10.

A mciroscope 30 with an eyepiece 32, is used for measuring the diameter of the interface between a less dense liquid (fluid) shown at 102 and a more dense liquid (fluid) 100 inside the rotating cylinder assembly 50. The microscope is mounted with its axis substantially perpendicular to the axis of the cylinder assembly 50 and the rod 52. The objective lens 36 is aligned by a vertical adjustment handle 38. As can best be seen in FIG. 3, the vertical adjustment handle 38 actuates an arm 40 vertically along a threaded shaft 42. The body tube 34 of the mircoscope 30 is connected to the arm 40 through a guide 41 which is fixed to arm 40 and permits horizontal movement of the telescope. The telescope is moved vertically as the arm 40 is actuated. The cylinder assembly is rotated at a selected speed until steady state equilibrium is achieved, causing the more dense liquid 100 (see FIG. 7) to be centrifuged to the outer portion of the cylinder assembly 50 while the less dense liquid 102 adheres to the tubular rod 52. The apparent diameter, $d_2$, of the interface 103 between the two liquids is measured while being viewed through lens 36.

The microscope may be moved parallel to the axis of the spinning rod on guides 41. By lining up a "hash mark" on the lens of the microscope with the outer surface of the liquid interface, after the cylinder assembly is spinning and then moving the telescope in direction along the axis of the rod, the operator can check whether equilibrium has been reached. When equilibrium is reached, the interface diameter will be substantially constant along the entire length of the rod. Only one reference mark on the lens is necessary for determining that equilibrium has been reached so long as the microscope moves parallel to the axis of rod 52. Traveling microscopes which move in two axes are well known.

A stroboscope 95 is used to enhance the visibility of the less desne liquid 102 and the measurement of the apparent diameter of the interface 103 formed therefrom. A stroboscope 95 is particularly helpful when the two liquids 100 and 102 are both transparent or similar colors. The stroboscope 95 is mounted near the cylinder assembly 50 and projects a stroboscope light on liquids 100 and 102 when steady state equilibrium is achieved.

Detailed views of the cylinder assebmly 50 are shown in FIGS. 4, 5, 6 and 7. The outer tube or cylinder 54 is made of a solid transparent material such as glass or plexiglass. The cylinder 54 is open at both ends, and has flanges 55A and 55B provided at opposite ends.

As shown in FIG. 4, the end cap 56 has a complemenatary flange 64 and is secured to the flange 55A to close a first end of the outer cylinder 54. An O-ring seal 61 is inserted into annular grooves in complementary surfaces between the flanges 55A and 64 for sealing. A spot face recess 57 is provided in the surface 56A of the end cap 56 facing the inner volume of the cylinder 54. A plug 58 having a conical tip 58A is mounted in the center of the recess 57 so that tip 58A faces into the cylinder 54. Bolts 62 extend through the flanges 55a and 64 and are secured by corresponding nuts 63 to hold the end cap 56 on the cylinder 54.

The tip 59 projects perpendicularly from the outer surface 56b of the end cap 56. The cylinder assembly 50 is put into place between the supports 27 and 23, by retracting the tip 25 of plunger 24 and placing tip 73 into recess 22a and then positioning the end of the cylinder assembly 50 in position so that tip 25 will fit into the cavity 60 under force of the spring 26. The end cap 56 and cylinder assembly 50 will rotate while supported on the plunger 24.

Loading cap 70 has a complementary flange 71 which is aligned with the flange 55B of the cylinder 54. Bolts 84 extend through the flanges 55B and 71 and are secured by corresponding nuts 85 to hold the loading cap 70 to the cylinder 54 to close the second end of the cylinder 54. An O-ring seal 83 is inserted into annular grooves in facing surface between the flanges 55b and 71 for sealing.

An internal bore 76 is provided in the loading cap 70 surface open to the inner surface 70A facing the cylinder 54. It is preferred that the circumference of the bore 76 be semicircular. A plunger 80 is slidably mounted in bore 76 and, as shown in FIG. 5, the cross section can be irregular to form a rotational drive between the plunger 80 and the bore 76. The inner rod 52 is fixed within a recess in the plunger 80 and extends to the opposite end of the cylinder 54. A coil spring 82 is inserted at the deepest point of the bore 76 and provides a force urging the plunger 80 toward the opposite end of the cylinder 54. As the plunger 80 is urged by the spring 82, the inner rod 52 is forced into contact with the plug 58. As shown in FIG. 4, the tip 58A of the plug 58 is received within the internal bore 52A of the rod 52 to seat the inner rod 52. The inner rod 52 achieves and maintains the same angular velocity as the outer cylinder 54 when the cylinder assembly 50 is rotated.

A pair of fill bores or passageways 74 are provided which extend from the outer surface 70B to the inner surface 70A of the loading cap 70. Threaded screws or plugs 75 are provided to seal the fill bores 74 after the fluids 100 and 102 have been filled into the cylinder 54.

When tip 73 and pin 77 are inserted into the recess 22A of shaft 20, any angular velocity of the shaft 20 is transmitted to the cylinder assembly 50. Stated in other words, after the pin 77 is locked on the shaft 20, the rotation of the shaft 20 causes the simultaneous rotation of the cylinder assembly 50.

In order to fill the cylinder assembly 50 with liquids, the cylinder assembly 50 is held so that the loading cap 70 is at the top end. The end cap 56 is secured to the outer cylinder 54 as described above. With the loading cap 70 removed, a predetermined volume of the more dense liquid 100 is poured into the cylinder 54. It is preferred that the more dense liquid substantially fill the volume of the cylinder 54. However, it is to be understood that while the proportions of the two liquids are not critical, the outer cylinder must be completely filled with the two liquids.

After the more dense fluid 100 has been loaded into the cylinder 54, the loading cap 70 is secured to the cylinder 54. As shown in FIG. 6, both screws 75 are removed from the fill bores 74 during the loading of the less dense liquid 102. The less dense liquid 102 is introduced in the fill bores 74 by a hypodermic needle 90. As the cylinder assembly 50 is filled, the less dense liquid 102 remains near the top of the cylinder 54. The less dense liquid 102 is added until the fill bores 74 are filled and all air has been removed from the cylinder 54. The screws 75 are carefully threaded into the fill bores 74 so that no air is allowed to enter the cylinder 54.

After both liquids 100 and 102 have been loaded into the cylinder 54, the cylinder assembly 50 is carefully placed between the supports 23 and 27 as described above, and the motor 10 is started, and gradually increased in speed. As the angular velocity of the shaft 20 is transmitted to the cylinder assembly 50, the more dense liquid 100 is centrifuged to the outer diameter portions of the cylinder 54.

The approprate speed of rotation is obtained by increasing the motor speed using speed control 17, until the length of the less dense liquid surrounding inner rod 52 is adequate to form a well defined interface 103 with the more dense liquid. The rotational speed is kept at a level less than the speed where the less dense liquid elongates sufficiently to strike both ends of the cylinder. The length of the less dense liquid along inner rod 52 increases with speed. Therefore, by selecting the speed the length and diameter of the less dense liquid can be controlled, and once the desired length is reached, the speed is left constant. The diameter of the interface 103 will stabilize after a short while, and at that time the liquids in the cylinder assembly have reached the steady state equilibrium.

At steady state equilibrium the less dense liquid 102 assumes a stable shape as it adheres to the inner rod 52 and interface 103 assumes a constant apparent diameter, $d_a$, as shown in FIG. 7. Diameter measurements of the interface 103 can then be made with sufficient accuracy using the microscope 30 as described above.

MATHEMATICAL CALCULATIONS

Figure 3:
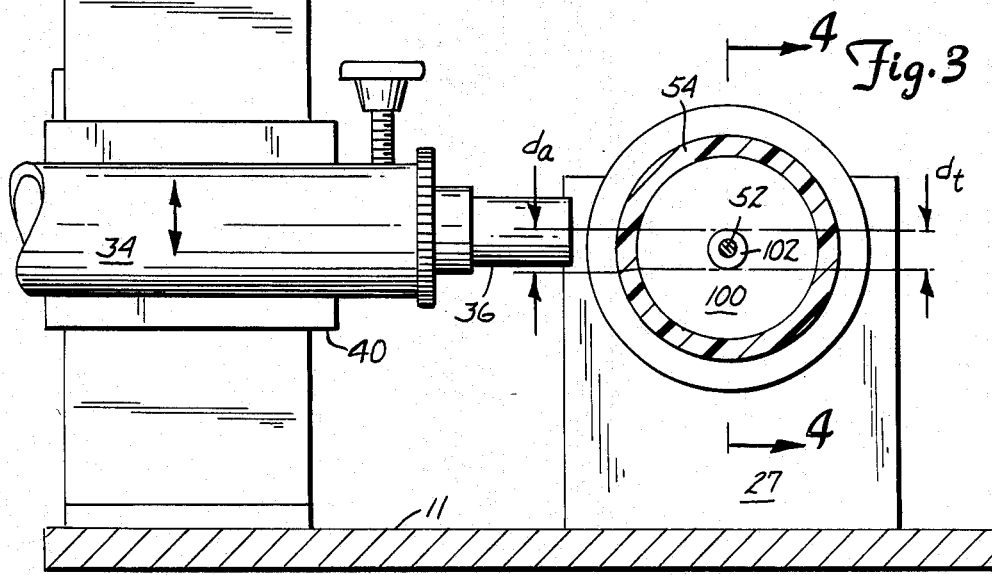
FIGS. 3 is a fragmentary sectional view taken along line 3—3 of FIG. 1.

Interfacial tension between the two liquids 100 and 102 is determined from the true diameter of the less dense liquid 102 measured after an appropriate steady state equilibrium has been achieved in the rotating cylinder assembly 50. The apparent diameter, $d_a$, of the less dense liquid 102, measured through the cylinder assembly 50 by the microscope objective lens 36, must be corrected for the lens distortion caused by the cylinder 54 and the more dense liquid 100 as shown in FIG. 3. Using the conventional thin lens theory, the true diameter, $d_t$, is calculated from the apparent diameter, $d_a$:

$$d_t = (n_3/n_1)d_a$$

where $n_1$ is the refractive index of the more dense fluid 100 and $n_3$ is the refractive index of air. For accurate interfacial tension measurements, the ratio of the true diameter to the diameter of the cylinder 54 should be less than 0.3.

The present spinning rod tensiometer measures the interfacial tension T between the more dense liquid 100 and the less dense liquid 102. The true diameter, $d_t$, is calculated as described above and the angular velocity $\Omega$ of the cylinder assembly 50 is simultaneously recorded. Interfacial tension T is calculated:

$$T = ([\rho]\Omega^2 r^3)/4$$

where $[\rho]$ is the difference in the density between the two fluids 100 and 102 and the $r = d_2/2$. As $\Omega$ is increased, $d_t$ decreases. Thus, different independent measurements of $d_t$ (and therefore the radius) are performed at various angular velocities to obtain an average value of T. Use of the above formula in calculating T requires that gravity be neglected. The conditions which permit the neglection of gravity are realized with the spinning rod tensiometer.

The spinning rod tensiometer 9 of the present invention teaches the use of a rotating rod 52 for forming a core in the less dense liquid 102, and is an improvement of spinning drop tensiometers. The rod 52 is important for several reasons. First, the lines of contact of the less dense liquid 102 on the rod 52 offer resistance to elongation. This attachment of the less dense liquid 102 creates an "artificial wall" and results in a more uniform apparent diameter $d_a$ at the selected speed. Second, the rod 52 reduces the spin-up time from rest to steady state equilibrium from hours to minutes. Third, the rod 52 eliminates the problem of positioning a drop of the less dense liquid in prior art. When the rod 52 starts spinning, the less dense liquid 102 is captured by the rod 52 and aligned nearly instantaneously. Fourth, the problems of liquid stability which plague prior art spinning drop tensiometers are completely eliminated by the spinning rod.

The proportions of the two liquids in the cylinder assembly 50 are not critical. Generally, it is convenient to have a large amount of more dense liquid 100 and a small amount of less dense liquid 102. The radii of the inner rod 52 and the outer cylinder 54 and the length of the outer cylinder 54 do not enter critically into the dynamics of the present invention and they may be selected for convenience of design. When using the above-described equation for determining T, it is important that the length of the less dense liquid 102 is shorter than the length of the cylinder 54 at the time $d_a$ measurements are recorded.

Although the present invention has been described with reference to preferred embodiments, workers skilled in the art will recognize that changes may be made in form and detail without departing from the spirit and scope of the invention.

What is claimed is:

1. An apparatus for measuring interfacial tension between two liquids of different densities spinning together in steady state equilibrium, said apparatus comprising:
   (a) an outer cylinder for receiving the liuqids, said outer cylinder having an internal chamber capable of being sealed at both ends;
   (b) a tubular rod having a diameter smaller than that of said outer cylinder, said rod being mounted within and along the longitudinal axis of said outer cylinder;
   (c) means for rotation said outer cylinder about its longitudinal axis in a horizontal manner at a constant rotational speed sufficient to maintain steady state equilibrium and to form a layer of the less dense liquid around said rod;
   (d) means for measuring the rotational speed of said outer cylinder when an appropriate steady state equilibrium exists between the liquids in the outer cylinder; and
   (e) means for measuring the diameter of the interface between the two liquids when an appropriate steady state equilibrium exists between the liquids.

2. The apparatus for measuring interfacial tension of claim 1 and including:
   (a) a first end sealing means for sealing a first end of said cylinder, said first end sealing means comprising means for permitting adding the less dense liquid; and
   (b) a second end sealing means for sealing a second end of said cylinder.

3. The apparatus for measuring interfacial tension of claim 2 wherein said first end sealing means comprises a loading cap having a plurality of fill bores, each fill bore having a means for sealing the fill bore after the less dense liquid has been added to said cylinder.

4. The apparatus for measuring interfacial tension of claim 3 wherein said loading cap comprises means for releasably supporting one end of the rod on said loading cap.

5. The apparatus for measuring interfacial tension of claim 4 wherein said second end sealing means comprises:
   (a) an end cap having a recess in the surface facing the interior volume of said cylinder; and
   (b) a plug secured to said recess and having a conical tip for receiving said rod.

6. The apparatus for measuring interfacial tension of claim 1 wherein said cylinder has a loading cap at one end and an end cap at the opposite end, and said means for rotating said cylinder about its longitudinal axis comprises:
   (a) first support means having a rotatable shaft mounted therein, a first end of said shaft having means for drivably engaging said loading cap;
   (b) second support means for rotatably mounting said end cap;
   (c) adjustable speed power means having a rotatable shaft; and
   (d) means for coupling said rotatable shaft of said power means with a second end of said shaft of said first support means;

whereby said cylinder is supported substantially horizontally between said first and second support means, respectively, and rotation of said rotatable shaft of said power means is transmitted by said coupling means to said shaft of said first support means and further transmitted to said cylinder by said means for drivably engaging.

7. The apparatus for measuring interfacial tension of claim 6 wherein the adjustable speed power means comprises an electric motor operated by a variable speed controller.

8. The apparatus for measuring interfacial tension of claim 6 wherein the means for drivably engaging comprises a drive slot in said first end of said shaft of said first support means for receiving a complementary drive pin mounted on said loading cap.

9. The apparatus for measuring interfacial tension of claim 6 wherein the means for measuring the rotational speed of said cylinder comprises:
   (a) a spur gear, axially mounted on said shaft of said power means;
   (b) a transducer mounted near said spur gear for sensing teeth on said spur gear and generating a corresponding electrical signal; and
   (c) a counter for receiving input signals from said transducer and displaying the speed of said shaft.

10. The apparatus for measuring the interfacial tension between two liquids of different densities as recited in claim 1, and including stroboscope means positioned near said cylinder and projecting an adjustable stroboscopic light on the fluids while steady state equilibrium exists between the fluids.

11. The apparatus for measuring the interfacial tension between two liquids of different densities as recited in claim 1 wherein said means for measuring the diameter of the less dense liquid includes a microscope mounted near and perpendicular to the longitudinal axis of said cylinder, said cylinder having substantially transparent outer walls.

12. A method of measuring the interfacial tension between two liquids of different densities comprising the steps of:
   (a) providing a cylinder having a rod of substantially smaller diameter than the cylinder mounted along the longitudinal axis of said cylinder;
   (b) filling two different liquids of different densities into said cylinder so that said cylinder is substantially filled, the volume of the less dense liquid being substantially less than the other liquid;
   (c) rotating said cylinder about its longitudinal axis at a desired angular velocity with the liquids contained therein until steady state equilibrium is achieved with a layer of the less dense liquid surrounding said rod;
   (d) determining the radius of the interface between the less dense liquid and the other liquid when steady state equilibrium; and (e) calculating the interfacial tension using the angular velocity and the radius of the interface determined.

13. The method of claim 12 wherein the step of determining the radius of the interface between the less dense liquid and the other liquid comprises measuring the apparent diameter of the interface while the cylinder is being rotated.

14. The method of claim 12 wherein the step of rotating the cylinder comprises rotating the cylinder about a substantially horizontal axis.

15. The method of claim 12 wherein the step of rotating said cylinder comprises rotating said cylinder at a speed wherein the less dense fluid forms an elongated interface with the other liquid in direction along the axis of the cylinder that is less than the length of the cylinder and wherein the diameter of the interface between the less dense liquid and the other liquid is substantially uniform along the length thereof.

* * * * *